(12) United States Patent
Fouchard et al.

(10) Patent No.: US 10,436,691 B2
(45) Date of Patent: Oct. 8, 2019

(54) METHOD OF ASSESSING ASPHALTENE INHIBITOR EFFICIENCY

(71) Applicant: ECOLAB USA INC., St. Paul, MN (US)

(72) Inventors: David Marc Daniel Fouchard, Sugar Land, TX (US); Jennifer Elaine Carmichael, Houston, TX (US)

(73) Assignee: ECOLAB USA INC., St. Paul, MN (US)

(*) Notice: Subject to any disclaimer, the term of this patent is extended or adjusted under 35 U.S.C. 154(b) by 0 days.

(21) Appl. No.: 15/400,489

(22) Filed: Jan. 6, 2017

(65) Prior Publication Data
US 2017/0115194 A1    Apr. 27, 2017

Related U.S. Application Data

(62) Division of application No. 14/197,853, filed on Mar. 5, 2014, now Pat. No. 9,574,981.

(60) Provisional application No. 61/791,737, filed on Mar. 15, 2013.

(51) Int. Cl.
| | |
|---|---|
| *C09K 8/524* | (2006.01) |
| *G01N 17/00* | (2006.01) |
| *G01N 33/28* | (2006.01) |
| *G01N 5/00* | (2006.01) |

(52) U.S. Cl.
CPC ............ *G01N 5/00* (2013.01); *C09K 8/524* (2013.01); *G01N 17/008* (2013.01); *G01N 33/2835* (2013.01)

(58) Field of Classification Search
CPC ........................................ G01N 5/00
USPC ........................................... 73/61.62
See application file for complete search history.

(56) References Cited

U.S. PATENT DOCUMENTS

| | | | |
|---|---|---|---|
| 4,767,545 A | 8/1988 | Karydas et al. | |
| 5,595,243 A * | 1/1997 | Maki, Jr. ............... | B08B 3/12 166/177.2 |
| 5,969,237 A | 10/1999 | Jones et al. | |
| 7,150,183 B2 | 12/2006 | Kharrat et al. | |

(Continued)

FOREIGN PATENT DOCUMENTS

| | | |
|---|---|---|
| EA | 000073 B1 | 6/1998 |
| RU | 2307860 C2 | 10/2007 |

(Continued)

OTHER PUBLICATIONS

Boek, Edo S., H.K. Ladva, J.P. Crawshaw, and J.T. Padding, "Deposition of Colloidal Asphaltene in Capillary Flow: Experiments and Mesoscropic Simulation," Energy & Fuels, 22 (2008) pp. 805-813.

(Continued)

*Primary Examiner* — Justin Seo
*Assistant Examiner* — Jean F Morello
(74) *Attorney, Agent, or Firm* — Eric D. Babych; Brinks Gilson & Lione

(57) ABSTRACT

Methods of assessing asphaltene inhibitor/dispersant efficiency are disclosed. Also disclosed are methods of assessing solvent/dispersant/cleaner efficacy for remediating asphaltene deposition. The methods are useful in facilitating the production, transportation, storage, and separation of crude oil and natural gas, and more particularly, for preventing the undesired deposition of asphaltene from crude oil.

11 Claims, 1 Drawing Sheet

(56) References Cited

U.S. PATENT DOCUMENTS

| | | | |
|---|---|---|---|
| 8,114,927 B1* | 2/2012 | Ahluwalia | C08L 95/005 106/273.1 |
| 2003/0079879 A1 | 5/2003 | Grainger et al. | |
| 2007/0240528 A1* | 10/2007 | Kranbuehl | G01N 17/00 73/866 |
| 2008/0020949 A1 | 1/2008 | Trimble et al. | |
| 2008/0134770 A1 | 6/2008 | Horsup | |
| 2010/0112378 A1* | 5/2010 | Deininger | C23C 8/02 428/702 |
| 2010/0314117 A1 | 12/2010 | Li et al. | |
| 2011/0056677 A1* | 3/2011 | Holderman | E21B 34/063 166/205 |
| 2011/0127031 A1* | 6/2011 | Zolezzi Garreton | E21B 28/00 166/249 |
| 2011/0162558 A1 | 7/2011 | Mena Cervantes et al. | |
| 2011/0203353 A1 | 8/2011 | Hough et al. | |
| 2011/0269650 A1 | 11/2011 | Hernandez Altamirano et al. | |
| 2015/0011453 A1* | 1/2015 | Bennett | C11D 3/2006 510/402 |
| 2015/0315520 A1* | 11/2015 | Eppler | A61Q 5/00 424/64 |

FOREIGN PATENT DOCUMENTS

| | | | |
|---|---|---|---|
| RU | 2429344 C1 * | 9/2011 | E21B 43/22 |
| WO | WO 96/0022451 A | 7/1996 | |

OTHER PUBLICATIONS

Boek, Edo S., A.D. Wilson, J.T. Padding, T.F. Headen, and J.P. Crawshaw, "Multi-scale Simulation and Experimental Studies of Asphaltene Aggregation and Deposition in Capillary Flow," Energy & Fuels, 24 (2010) pp. 2361-2368.

Broseta, D., M. Robin, T. Savvidis, C. Féjean, M. Durandeau, and H. Zhou, "Detection of Asphaltene Deposition by Capillary Flow Measurements," Society of Petroleum Engineers, SPE 59294, 9 pages.

Wang, Jianxin, J.S. Buckley, and J.L. Creek, "Asphaltene Deposition on Metallic Surfaces," Journal of Dispersion Science and Technology, 25(3), (2004) pp. 287-298.

\* cited by examiner

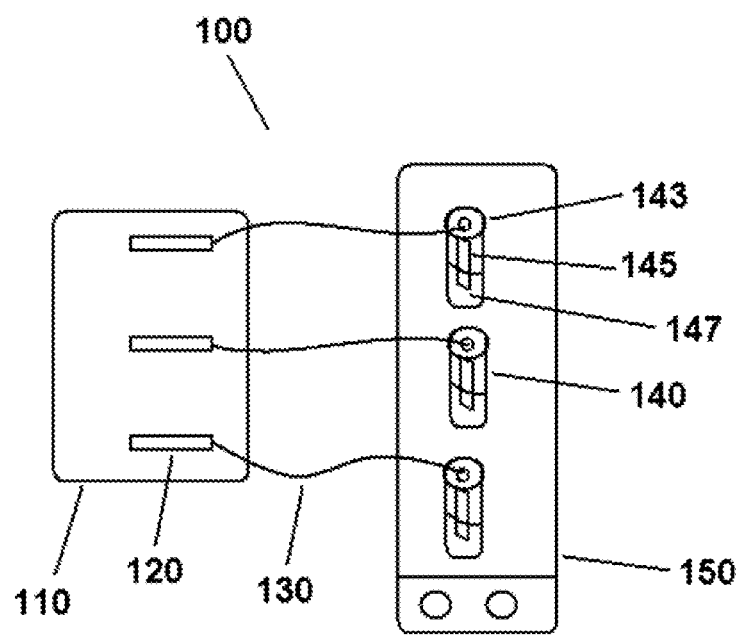

METHOD OF ASSESSING ASPHALTENE INHIBITOR EFFICIENCY

TECHNICAL FIELD

The present disclosure relates generally to methods of assessing asphaltene inhibitor/dispersant efficiency in crude oil applications.

BACKGROUND

Crude oil from geological formations commonly contains solids, typically as one or more of waxes, asphaltenes, sulfur, minerals (e.g., scale), and hydrates. When crude oil is transported via pipeline, e.g., from a geological formation to a wellhead or from a wellhead or a storage vessel to a refinery via pipeline, changes in the pressure, temperature, composition, etc. (or other parameters of the flowing crude oil) can lead to deposition of solids on the pipe walls and surfaces. The deposition of these solids from the crude oil onto the interior surfaces of the pipes can have a drastic and negative impact on the oil flow through these pipes.

Asphaltenes, in particular, make up one of the most polar fractions of crude oil, and often will precipitate and deposit on pipe surfaces upon an external stress, such as temperature, pressure and/or compositional changes in the oil (resulting from blending or physical/chemical processing). Asphaltene deposits can plug downhole tubulars, wellbores, choke off pipes and interfere with the functioning of separator equipment.

Traditionally, in the petroleum industry, the problems caused by the deposition of asphaltenes have been controlled by use of asphaltene inhibitors and/or dispersants. Assessment of inhibitor effectiveness has traditionally included down-hole processes, complicated and/or costly lab techniques or non-deposition based methods. Screening through such processes is generally slow and only allows for the screening of one or a few asphaltene inhibitors at a time, or possibly even irrelevant when precipitation-based methods are used. The depositions methods developed to date are too cumbersome and/or costly to make high throughput screening practical.

The asphaltene dispersancy test is currently the industry standard for asphaltene inhibitor evaluation and selection. The test, however, is a precipitation test and gives no information about deposition. Other available tests are expensive for even a single data point, require large quantities of crude oil, and/or take at least several hours to complete. Thus, there exists a need for a reliable, fast, and cost-effective method to assess asphaltene inhibitor efficacy.

SUMMARY

In one aspect, disclosed is a method of assessing asphaltene inhibitor/dispersant efficacy in a crude oil, the method comprising: a) weighing a first coupon; immersing the first coupon or a portion thereof into a first sample for a first selected time period, the first sample comprising an aliquot of the crude oil; adding a precipitant to the first sample within the first selected time period; removing the first coupon from the first sample at the end of the first selected time period; and drying and weighing the first coupon; b) weighing a second coupon; immersing the second coupon or a portion thereof into a second sample for a second selected time period, the second sample comprising an aliquot of the crude oil and an asphaltene inhibitor/dispersant; adding a precipitant to the second sample within the second selected time period; removing the second coupon from the second sample at the end of the second selected time period; and drying and weighing the second coupon; c) determining the weight of asphaltenes deposited on the first coupon and the weight of asphaltenes deposited on the second coupon; and d) determining the % asphaltene deposition inhibition via equation (1), $$\% \text{ Inhibition} = 100 \times \left(1 - \frac{\text{Weight of apshaltenes deposited on the second coupon}}{\text{Weight of asphaltenes deposited on the first coupon}}\right). \quad (1)$$

In certain embodiments, after the coupons are removed from respective samples and dried, the coupons are rinsed (e.g., with heptane), the rinsed coupons dried, and then weighed.

In certain embodiments, the volume of crude oil in the first sample ranges from 5-20 mL, and the volume of crude oil in the second sample ranges from 5-20 mL. The volume used for each sample is preferably equal.

In certain embodiments, the first selected time period ranges from 1 hour to 33 days, and the second selected time period ranges from 1 hour to 33 days. In a preferred embodiment, the first selected time period and the second selected time period are of the same or substantially the same duration.

In some embodiments, each of step a) and step b) individually comprise three sequential events: precipitant addition, soak time after precipitant addition, and drying time after soaking. The three events may have the following length: precipitant addition time, >0 min to 48 hours; soak time, 30 min to 30 days; and dry time, 1 hour to 48 hours. In certain embodiments, the events have the following length: precipitant addition time, 3 hours; soak time, 48 hours; and dry time, 24 hours. In some aspects, the same event occurring in each of steps a) and b) is of the same or substantially the same duration (e.g., the precipitant addition time is the same or substantially the same in each of steps a) and b)). For step a), it is to be understood that the events of precipitant addition and soak time occur in the first selected time period; and for step b), it is to be understood that the events of precipitant addition and soak time occur in the second selected time period.

In another embodiment, after the sequential steps of precipitant addition, soak time after precipitant addition, and drying time after soaking, the following sequential steps occur: rinsing of the coupons (e.g., with heptane), drying of the rinsed coupons, and weighing of the rinsed and dried coupons.

In certain embodiments, the volume of precipitant added to each of the first and second samples is determined by titration of the crude oil with the precipitant prior to assessing the asphaltene inhibitor/dispersant efficacy. In certain embodiments, the volume of precipitant added to each of the first and second samples corresponds to the Onset Volume±20%. In certain embodiments, the precipitant is added dropwise to each of the first and second samples over the first and second selected time periods. In certain embodiments, the precipitant is added in fractions to each of the first and second samples over the first and second selected time periods. In certain embodiments, the precipitant is added all at once to each of the first and second samples over the first and second selected time periods.

In certain embodiments, steps a) and b) are conducted in parallel such that the first and second selected time periods are of the same or substantially the same duration and occur together in real time.

In certain embodiments, the first sample and the second sample are each substantially closed to the atmosphere during the first and second selected time periods.

In certain embodiments, each of the first and second samples are stirred or agitated during at least a portion of the first and second selected time periods.

In certain embodiments, the asphaltene inhibitor/dispersant is selected from the group consisting of aliphatic sulphonic acids; alkyl aryl sulphonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, polyisobutylene succinic anhydride; and combinations thereof.

In certain embodiments, the precipitant is a liquid precipitant selected from the group consisting of alkane solvents. In certain embodiments, the liquid precipitant is heptanes, hexanes, pentanes, or any combination thereof.

In certain embodiments, the precipitant is a gas precipitant selected from the group consisting of methane, ethane, propane, butane, carbon dioxide, nitrogen, argon, helium, neon, krypton, xenon, and any combination thereof.

In certain embodiments, each sample is heated to a temperature of −15° C. to +80° C. In some embodiments, each sample may be heated to a temperature of −15° C. to +300° C. In certain embodiments, each sample is under a pressure of atmospheric to 20,000 psi. In some embodiments, each sample is under a pressure of atmospheric to 30,000 psi. In certain embodiments, each sample is at ambient temperature and pressure.

In certain embodiments, each sample further comprises one or more constituents selected from the group consisting of paraffin inhibitors, corrosion inhibitors, scale inhibitors, emulsifiers, water clarifiers, dispersants, emulsion breakers, hydrogen sulfide scavengers, gas hydrate inhibitors, biocides, pH modifiers, surfactants, brine, water, and solvents.

In certain embodiments, the coupons are carbon steel coupons, iron coupons, stainless steel coupons, glass coupons, coupons comprised of synthetic or natural polymers, coupons comprised of any metal, coupons comprised of any mineral, coupons comprised of wood, or any combination thereof. In a preferred embodiment, the coupons are carbon steel or stainless steel.

In certain embodiments, the coupons are cylindrical coupons, rectangular prism coupons, spherical coupons, or hexagonal prism coupons.

In certain embodiments, the method is carried out on-site at an oil field.

In another aspect, disclosed is a method of assessing a solvent efficacy for remediating asphlatene deposition, comprising: a) providing a coupon having asphaltene deposit, said coupon optionally provided by the precipitation/soaking procedure described herein; b) weighing the coupon; c) immersing the coupon in a solution comprising at least one solvent, wherein the coupon is immersed for a selected time period; d) removing the coupon from the solution at the end of the selected time period, and drying and weighing the coupon; and e) determining the % asphaltene deposition removal via equation (2), $$\% \text{ Removal} = 100 \times \left(1 - \frac{\text{Weight of apshaltenes on coupon after immersing}}{\text{Weight of asphaltenes on coupon before immersing}}\right). \qquad (2)$$

In certain embodiments, after the coupon is removed from the solution and dried, the coupon is rinsed, the rinsed coupon dried, and then weighed. In other embodiments, the coupon may be removed and the deposit may be isolated for further analysis using other analytical methods to qualify and quantify the deposit.

In certain embodiments, the solvent is selected from aromatic solvents such as toluene, xylene, benzene, and HAN (heavy aromatic naphtha). In certain embodiments, any solvent in which asphaltenes are soluble can be used, or any combination thereof. In addition, the solvents can be used in conjunction with a variety of dispersants (surface active agents).

BRIEF DESCRIPTION OF THE DRAWINGS

FIG. 1 depicts an exemplary setup useful for assessing the efficacy of asphaltene inhibitors/dispersants at preventing and/or reducing deposition of asphaltenes.

DETAILED DESCRIPTION

Disclosed herein are methods for assessing the efficacy of asphaltene inhibitors/dispersants at preventing and/or reducing deposition of asphaltenes from a liquid (e.g., crude oil). The efficiency of asphaltene inhibitors/dispersants is assessed by comparing the mass of asphaltenes deposited on a coupon in the presence and absence of inhibitors/dispersants. Also disclosed herein are methods for designing a cleaning program to remediate an asphaltene deposition problem in the field. A deposition test can be conducted in multiplicate using untreated (oil), and the resulting asphaltene deposit coated coupons can be used in a second experiment aimed at assessing the cleaning power of a variety of solvent-dispersant/cleaner packages.

The disclosed methods provide several advantages over currently available screening methods. Specifically, the methods are inexpensive, convenient, and reliable compared to currently available technologies. The methods can be used to rapidly screen a large number of samples, and have the flexibility to account for changing field parameters on a case by case basis (e.g., the effects of gas composition, shear rate, and temperature). The methods can be used to collect a multitude of data points in a short time period (e.g., 4 hours) and require a minimal volume of liquid per data point (e.g., 5-20 mL of crude oil).

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising", "consisting of" and "consisting essentially of," the embodiments or elements presented herein, whether explicitly set forth or not.

"Asphaltene inhibitor/dispersant," as used herein, refers to a chemical or composition that prevents or reduces asphaltene precipitation from a crude oil and/or deposition of asphaltene on surfaces in contact with a crude oil, or a chemical used to help in the removal of an asphaltene deposit already formed on a surface.

"Deposition," as used herein, refers to the coating of agglomerated materials on the surface of a material, such as an interior wall of a pipe or tubing.

"Precipitant," as used herein, refers to a liquid or gas that triggers asphaltene destabilization from crude oil.

"Precipitation," as used herein, refers to the agglomeration of solids which may remain suspended in the bulk fluid fraction, or settle down by gravity, but do not physically attach to any surface.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. METHOD OF ASSESSING ASPHALTENE INHIBITOR/DISPERSANT EFFICACY

In one aspect, disclosed herein are methods for assessing the efficacy of asphaltene inhibitors/dispersants at preventing and/or reducing deposition of asphaltenes from a liquid (e.g., crude oil). The efficiency of asphaltene inhibitors/dispersants is assessed by comparing the mass of asphaltenes deposited on a coupon in the presence and absence of inhibitors/dispersants. The deposition may be triggered by addition of a precipitant to the liquid sample.

In general, to conduct an efficiency test of an asphaltene inhibitor/dispersant with a particular crude oil, a coupon is immersed in one container containing crude oil and a stir bar, and another coupon is immersed in a second container containing crude, a stir bar, and the asphaltene inhibitor/dispersant to be evaluated. A liquid precipitant or gas precipitant is then added to the crude oil in each container in order to trigger asphaltene deposition on the coupon surface.

At the end of the experiment, the asphaltene tarred coupons are removed from the crude/precipitant mixture, dried, and weighed. Optionally, the coupons are rinsed and dried before being weighed. The amount of asphaltenes precipitated at the surface of the coupon is determined by comparing the weight of the coupon before the experiment to the weight at the end of the experiment. The weight of asphlatenes collected on the coupon surface for a treated oil (i.e., oil dosed with an asphaltene inhibitor/dispersant) is compared with that of an untreated oil. From these two values, the inhibitor/dispersant efficiency is assessed using the following formula:

$$\% \text{ Inhibition} = 100 \times \left(1 - \frac{\text{Weight of apshaltenes deposited from treated sample}}{\text{Weight of asphaltenes deposited from blank}}\right)$$

The amount of asphlatene deposited onto the coupon depends upon the efficacy of the asphaltene inhibitor. An efficient and effective asphaltene inhibitor will result in less asphaltene mass deposited from the treated samples and result in a higher % inhibition number from the equation above. In turn, an ineffective or non-efficient or poor asphaltene inhibitor will result in an amount of asphaltene amount or weight deposited to the coupon that is closer to the weight of the control coupon (i.e., the coupon that has been placed in the container with no asphaltene inhibitor).

During the experiment, the precipitant can be added in any selected fashion (e.g., drop wise, all at once, or in several fractions over the duration of the experiment). A suitable amount of precipitant to be added to the crude oil during the experiment can be determined by titration of the oil with the precipitant prior to starting the experiment. The amount of precipitant necessary to initiate asphaltene precipitation (called Onset Volume) is used as a guideline for the total amount of precipitant to be added to the oil during the deposition test. Generally, a volume of precipitant corresponding to the Onset Volume±20% will be used during the deposition test.

The duration of the experiment can be conducted over any selected time period. In certain embodiments, the time ranges from minutes to days (e.g., 1 hour to 33 days). Preferably, the experiment includes the sequential steps of precipitant addition, soaking after precipitant addition, and drying. The three events may have the following length: precipitant addition, >0 min to 48 hours (e.g., 3 h); soak time, 30 min to 30 days (e.g., 48 h); and dry time, 1 hour to 48 hours (e.g., 24 h). In some aspects, the same events in each of steps a) and b) are of the same or substantially the same duration (e.g., the precipitant addition time is the same or substantially the same in steps a) and b); preferably the soak time is the same or substantially the same in steps a) and b); and the drying time following the soak time may be the same or substantially the same in steps a) and b)).

For step a), it is to be understood that the events of precipitant addition and soak time occur in the first selected time period; and for step b), it is to be understood that the events of precipitant addition and soak time occur in the second selected time period.

In another embodiment, after the sequential steps of precipitant addition, soak time after precipitant addition, and drying time after soaking, the following sequential steps occur: rinsing of the coupons (e.g., with heptane), drying of the rinsed coupons, and weighing of the rinsed and dried coupons.

In certain embodiments, the deposition tests on treated and untreated samples are conducted simultaneously in parallel to limit experimental errors. In some embodiments, the containers of crude oil with the immersed coupons are kept closed to the atmosphere as well as possible during the entire addition of precipitant to avoid evaporation and loss of crude or precipitant.

The tests can be conducted at any selected temperature, agitation, and pressure to simulate field conditions. In certain embodiments, the tests are conducted at ambient temperature and pressure. In certain embodiments, the tests are conducted at non-ambient temperature and pressure. In certain embodiments, the tests are conducted at −15 to +80° Celsius; atmospheric to 20,000 psi; shear 0 to 10000 Pascals. In some embodiments, the tests are conducted at −15 to +300° Celsius; atmospheric to 30,000 psi; shear 0 to 10000 Pascals.

Suitable liquid precipitants include alkane solvents (e.g., heptanes, hexanes, pentanes or any liquid alkane, branched, cyclic or linear).

Suitable gas precipitants include methane, ethane, propane, butane, carbon dioxide, nitrogen, argon, helium, neon, krypton, and xenon.

Suitable asphaltene inhibitors/dispersants that can be evaluated include, but are not limited to, aliphatic sulphonic acids; alkyl aryl sulphonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

FIG. 1 shows an exemplary device configuration useful for assessing the efficacy of asphaltene inhibitors/dispersants at preventing and/or reducing deposition of asphaltenes from a liquid (e.g., crude oil). The setup may be used to test the inhibitor/dispersant at atmospheric pressure and temperature, or may be adapted to be a pressurized and temperature controlled apparatus. As shown, the setup 100 includes a syringe pump 110 used to inject an exact same amount of precipitant at an exact same time to each of the vials 140. The setup further includes syringes 120 containing a precipitant to be added to the vials 140. The precipitant is added to the vials via tubing 130 (e.g., PEEK tubing). The vials 140 each include a vial cap 143 that holds a test coupon 145, which is immersed in a crude oil-precipitant mixture 147. The vials are each equipped with a stir bar, which is controlled by a stir plate 150 that controls the shear inside the vials. The setup may be adapted to test more or less samples from that depicted by using additional or fewer syringes and vials, for example.

3. METHOD OF ASSESSING CLEANING PROGRAM TO REMEDIATE AN ASPHLATENE DEPOSITION

In another aspect, disclosed is a method of assessing a solvent efficacy for remediating asphlatene deposition. The method can be used to design a cleaning program to remediate an asphlatene deposition problem in the field.

In one exemplary embodiment, a deposition test would be conducted in multiplicate using untreated (oil), and the resulting asphaltene deposit coated coupons used in a second experiment aimed at assessing the cleaning power of a variety of solvent-dispersant/cleaner packages. The asphaltene coated coupons can be immersed in agitated cleaner solutions and the kinetics of dissolution assessed for each solvent in order to pick the best possible solvent for the remediation job.

In certain embodiments, the solvent is selected from aromatic solvents such as toluene, xylene, benzene, and HAN (heavy aromatic naphtha). In certain embodiments, the solvent may be any solvent in which asphaltenes are soluble, or a combination thereof. In addition, the solvents can be used in conjunction with a variety of dispersants (surface active agents).

4. EXAMPLES

The foregoing may be better understood by reference to the following examples, which are intended for illustrative purposes and are not intended to limit the scope of the invention.

Example

The following example describes an actual experiment that was conducted with the disclosed method using a setup according to FIG. 1. All data and results were collected and obtained via the procedure described. The objective of the experiment described was to evaluate and compare the performance of four Inhibitors (A, B, C, and D), when used to treat a sample of crude oil from the Gulf of Mexico (GOM crude oil).

Equipment & Materials

The following equipment and materials were used: Analytical Balance; Multicapacity delivery syringe pump; Multi-position magnetic stirrer (10-channel); Dropper pipette; Cylindrical glass vials with customized caps (quantity: 10); Syringes (quantity: 10); Attachable syringe needles with PEEK tubing (quantity: 10); Small magnetic stir bars (quantity: 10); Metal coupons (quantity: 10); GOM oil sample (130 mL); Heptane (excess); and Inhibitors (A, B, C, and D).

Experimental Procedure

Prior to performing the experiment, the precipitant onset volume for the oil sample designated for testing was determined, using heptane solvent as the liquid precipitant. The measured onset volume was approximately 51% dilution with heptane for the GOM oil sample. The test sample components were then determined based on this value.

To prepare the test equipment for this experiment, the mass of ten clean steel coupons was measured and recorded for each. The syringes to be used for heptane delivery were then assembled using PEEK tubing and needle attachments, followed by withdrawing 17 mL heptane into each syringe. Any visible air was removed from all syringes to ensure accurate and uniform volume delivery, and then all ten syringes were secured onto the pump rack.

The test samples were prepared by first distributing 13 mL GOM crude oil to each of ten glass sample vials, followed by injection of Inhibitor to the appropriate vials, as indicated in Table 1.

TABLE 1

Inhibitor Treatment of Samples

| Sample No. | Inhibitor (1000 ppm) |
| --- | --- |
| 1 | Untreated |
| 2 | Untreated |
| 3 | Inhibitor A |
| 4 | Inhibitor A |

TABLE 1-continued

Inhibitor Treatment of Samples

| Sample No. | Inhibitor (1000 ppm) |
|---|---|
| 5 | Inhibitor B |
| 6 | Inhibitor B |
| 7 | Inhibitor C |
| 8 | Inhibitor C |
| 9 | Inhibitor D |
| 10 | Inhibitor D |

After Inhibitor dosing was completed, a magnetic stir bar was added to each sample vial, followed by the attachment of each metal coupon to the inside of the appropriate vial cap. The coupon-cap assemblies were then carefully affixed onto the corresponding sample vials, allowing the coupons to become submerged into the sample fluid. Once the caps were tightly secured, the sample vials were positioned onto the 10-channel magnetic stirrer, followed by activation of the stirrer (approx. 180 rpm). The PEEK tubing of the pre-filled syringes was then inserted into the cap of each sample vial, and adjusted to ensure uniform positioning and airtight. To initiate the experimental run, the syringe pump was programmed to deliver a volume of 17 mL (per syringe), at a rate of 3 mL per hour, resulting in a heptane addition time of 5.67 hours.

Once heptane delivery was completed, the assembly was left for an additional 144 hours, allowing the coupons to soak in the sample fluid with continued agitation (approx. 180 rpm). After completion of the soak period, the stir agitation was halted and each coupon-cap assembly was cautiously removed from the sample vials, avoiding any contact between coupons and the vial wall. The coupons were then detached from the vial caps, and allowed to air-dry for 24 hours. Once dry, each coupon was individually rinsed with heptane solvent, using a dropper pipette. The coupons were rinsed in a drop-wise manner until no visible oil discoloration was present in the wash solvent, then allowed to dry for 5 minutes. The mass of each coupon was then measured and recorded.

Data and Results

To determine the mass of deposit obtained on each coupon, the initial coupon mass was subtracted from the final coupon mass. Inhibition was determined using Equation 1, where the denominator is the mean of the deposit mass obtained on both untreated sample coupons. The results are reported below in Table 2. Each condition was run in duplicate for repeatability evaluation.

$$\% \text{ Inhibition} = 100 \times \left( 1 - \frac{\text{Mass of apshaltenes deposited on coupon from treated sample}}{\text{Mean mass of apshaltenes deposited on coupon from untreated sample}} \right) \quad \text{(Equation 1)}$$

TABLE 2

Mass Results of Asphaltene Deposits on Coupons

| Sample No. | Inhibitor (1000 ppm) | Deposit Mass (g) | Inhibition (%) |
|---|---|---|---|
| 1 | Untreated | 0.0145 | NA |
| 2 | Untreated | 0.0112 | NA |
| 3 | Inhibitor A | 0.0085 | 33.85 |

TABLE 2-continued

Mass Results of Asphaltene Deposits on Coupons

| Sample No. | Inhibitor (1000 ppm) | Deposit Mass (g) | Inhibition (%) |
|---|---|---|---|
| 4 | Inhibitor A | 0.0094 | 26.85 |
| 5 | Inhibitor B | 0.0066 | 48.64 |
| 6 | Inhibitor B | 0.0068 | 47.08 |
| 7 | Inhibitor C | 0.0079 | 38.52 |
| 8 | Inhibitor C | 0.0081 | 36.96 |
| 9 | Inhibitor D | 0.0049 | 61.87 |
| 10 | Inhibitor D | 0.0050 | 61.09 |

CONCLUSION

Based on the results obtained, the most effective Inhibitor for the GOM oil sample was Inhibitor D, which resulted in greater inhibition than all other samples for both duplicate test samples. The results also indicate that Inhibitor A is the least effective Inhibitor for the GOM oil sample, since both samples treated with this Inhibitor displayed the least inhibition of all other treated samples. The results do indicate that all coupons of samples treated with an Inhibitor obtained less asphaltene deposit (mass) than the coupons of untreated samples. Thus, the disclosed method is useful for assessing asphaltene inhibitor/dispersant efficiency in crude oil applications.

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. Any and all patents, patent applications, scientific papers, and other references cited in this application, as well as any references cited therein, are hereby incorporated by reference in their entirety. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A method of assessing a solvent efficacy for remediating asphaltene deposition, comprising:
    submerging a clean coupon into crude oil;
    adding a precipitant to the crude oil to promote deposition of asphaltene onto the clean coupon:
    removing the coupon from the crude oil;
    drying the coupon:
    weighing the coupon;
    immersing the coupon in a solution comprising at least one solvent, wherein the coupon is immersed for a selected time period, wherein a dispersant is added to the solvent;

removing the coupon from the solution at an end of the selected time period, and drying and weighing the coupon; and determining % asphaltene deposition removal via equation (2), $$\% \text{ Removal} = 100 \times \left(1 - \frac{\text{Weight of asphaltenes on coupon after immersing}}{\text{Weight of asphaltenes on coupon before immersing}}\right); \quad (2)$$

assessing the solvent efficacy for remediating asphaltene deposition based on the % asphaltene deposition removal.

2. The method of claim 1, wherein the dispersant is selected from the group consisting of aliphatic sulphonic acids; alkyl aryl sulphonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, polyisobutylene succinic anhydride, and any combination thereof.

3. The method of claim 1, wherein the solvent is an aromatic solvent.

4. The method of claim 1, wherein the solvent is selected from the group consisting of toluene, xylene, benzene, and heavy aromatic naphtha.

5. The method of claim 1, wherein the coupon is a glass coupon.

6. The method of claim 1, wherein the immersing of the coupon is conducted at a pressure of 20,000 psi to 30,000 psi.

7. The method of claim 1, wherein the coupon is made of synthetic or natural polymer.

8. The method of claim 1, wherein the solution has a temperature of 80° C. to 300° C.

9. A method of assessing a solvent efficacy for remediating asphaltene deposition, comprising:

submerging a clean coupon into crude oil;

adding a precipitant to the crude oil to promote deposition of asphaltene onto the clean coupon:

removing the coupon from the crude oil;

drying the coupon:

weighing the coupon;

immersing the coupon in a solution comprising at least one solvent, wherein the coupon is immersed for a selected time period, wherein a dispersant is added to the solvent, wherein the solution has a temperature of 300° C.;

removing the coupon from the solution at an end of the selected time period, and drying and weighing the coupon; and determining % asphaltene deposition removal via equation (2), $$\% \text{ Removal} = 100 \times \left(1 - \frac{\text{Weight of asphaltenes on coupon after immersing}}{\text{Weight of asphaltenes on coupon before immersing}}\right); \quad (2)$$

assessing the solvent efficacy for remediating asphaltene deposition based on the asphaltene deposition removal.

10. The method of claim 9, wherein the coupon is a glass coupon.

11. The method of claim 9, wherein the coupon is a glass coupon or is made of synthetic or natural polymer.

* * * * *

UNITED STATES PATENT AND TRADEMARK OFFICE
CERTIFICATE OF CORRECTION

PATENT NO. : 10,436,691 B2
APPLICATION NO. : 15/400489
DATED : October 8, 2019
INVENTOR(S) : David Marc Daniel Fouchard et al.

It is certified that error appears in the above-identified patent and that said Letters Patent is hereby corrected as shown below:

On the Title Page

Column 2, Line 3, item (56), under "Other Publications", please delete "Mesoscropic" and replace with --Mesoscopic--.

Column 2, Line 4, item (57), under "Abstract", please delete "asphlatene" and replace with --asphaltene--.

In the Claims

Column 12, Claim 9, Line 34 (approx.), after "the" please insert --%--.

Signed and Sealed this
Seventh Day of April, 2020

Andrei Iancu
*Director of the United States Patent and Trademark Office*